US008401608B2

(12) United States Patent
Baker, Jr. et al.

(10) Patent No.: US 8,401,608 B2
(45) Date of Patent: Mar. 19, 2013

(54) METHOD OF ANALYZING PHOTON DENSITY WAVES IN A MEDICAL MONITOR

(75) Inventors: Clark R. Baker, Jr., Newman, CA (US); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 840 days.

(21) Appl. No.: 12/570,394

(22) Filed: Sep. 30, 2009

(65) Prior Publication Data

US 2011/0077485 A1    Mar. 31, 2011

(51) Int. Cl.
*A61B 5/1455* (2006.01)

(52) U.S. Cl. .................. 600/323; 600/310; 600/476

(58) Field of Classification Search ............... 600/310, 600/322, 323, 336, 473, 476
See application file for complete search history.

(56) References Cited

U.S. PATENT DOCUMENTS

| | | |
|---|---|---|
| 3,638,640 A | 2/1972 | Shaw |
| 4,936,679 A | 6/1990 | Mersch |
| 4,971,062 A | 11/1990 | Hasebe et al. |
| 4,974,591 A | 12/1990 | Awazu et al. |
| 5,028,787 A | 7/1991 | Rosenthal et al. |
| 5,065,749 A | 11/1991 | Hasebe et al. |
| 5,084,327 A | 1/1992 | Stengel |
| 5,275,159 A | 1/1994 | Griebel |
| 5,353,799 A | 10/1994 | Chance |
| 5,416,582 A | 5/1995 | Knutson et al. |
| 5,424,843 A | 6/1995 | Tromberg et al. |
| 5,441,054 A | 8/1995 | Tsuchiya |
| 5,477,051 A | 12/1995 | Tsuchiya |
| 5,483,646 A | 1/1996 | Uchikoga |
| 5,492,118 A | 2/1996 | Gratton et al. |
| 5,497,769 A | 3/1996 | Gratton et al. |
| 5,555,885 A | 9/1996 | Chance |
| 5,730,124 A | 3/1998 | Yamauchi |
| 5,772,587 A | 6/1998 | Gratton et al. |
| 5,779,631 A | 7/1998 | Chance |
| 5,813,988 A | 9/1998 | Alfano et al. |
| 5,818,583 A | 10/1998 | Sevick-Muraca et al. |
| 5,830,139 A | 11/1998 | Abreu |

(Continued)

FOREIGN PATENT DOCUMENTS

| | | |
|---|---|---|
| DE | 19640807 | 9/1997 |
| EP | 0630203 | 12/1994 |

(Continued)

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

(Continued)

*Primary Examiner* — Eric Winakur
(74) *Attorney, Agent, or Firm* — Fletcher Yoder

(57) ABSTRACT

A monitoring system that may include an emission feature capable of emitting light into tissue, a modulator capable of modulating the emitter at a modulation frequency generally in a range of about 50 MHz to 3.0 GHz to generate resolvable photon density waves, a detection feature capable of detecting photons of the photon density waves after passage through the tissue and capable of providing a distribution of detected photons over a time period for the photon density waves, and a processor capable of calculating a skewness of the distribution and making determinations relating to a value of a physiologic parameter of the tissue based at least in part on the skewness of the distribution.

20 Claims, 6 Drawing Sheets

U.S. PATENT DOCUMENTS

| | | | |
|---|---|---|---|
| 5,831,598 A | 11/1998 | Kauffert et al. | |
| 5,855,205 A | 1/1999 | Papaionnou | |
| 5,859,713 A | 1/1999 | Khoury et al. | |
| 5,871,442 A | 2/1999 | Madarasz et al. | |
| 5,873,821 A | 2/1999 | Chance et al. | |
| 6,035,223 A * | 3/2000 | Baker, Jr. | 600/323 |
| 6,058,324 A * | 5/2000 | Chance | 600/473 |
| 6,064,917 A | 5/2000 | Matson | |
| 6,075,610 A | 6/2000 | Ueda et al. | |
| 6,081,742 A | 6/2000 | Amano et al. | |
| 6,120,460 A | 9/2000 | Abreu | |
| 6,124,597 A * | 9/2000 | Shehada et al. | 600/323 |
| 6,134,460 A | 10/2000 | Chance | |
| 6,192,261 B1 | 2/2001 | Gratton et al. | |
| 6,272,367 B1 | 8/2001 | Chance | |
| 6,285,895 B1 | 9/2001 | Ristolainen et al. | |
| 6,291,824 B1 | 9/2001 | Battarbee et al. | |
| 6,304,771 B1 | 10/2001 | Yodh | |
| 6,312,393 B1 | 11/2001 | Abreu | |
| 6,335,792 B1 | 1/2002 | Tsuchiya | |
| 6,353,750 B1 | 3/2002 | Kimura et al. | |
| 6,415,236 B2 | 7/2002 | Kobayashi et al. | |
| 6,419,671 B1 | 7/2002 | Lemberg | |
| 6,453,183 B1 | 9/2002 | Walker | |
| 6,461,305 B1 | 10/2002 | Schnall | |
| 6,487,439 B1 | 11/2002 | Skladnev et al. | |
| 6,516,214 B1 | 2/2003 | Boas | |
| 6,542,772 B1 | 4/2003 | Chance | |
| 6,544,193 B2 | 4/2003 | Abreu | |
| 6,549,284 B1 | 4/2003 | Boas et al. | |
| 6,549,795 B1 | 4/2003 | Chance | |
| 6,577,884 B1 | 6/2003 | Boas | |
| 6,591,122 B2 | 7/2003 | Schmitt | |
| 6,606,509 B2 | 8/2003 | Schmitt | |
| 6,618,042 B1 | 9/2003 | Powell | |
| 6,622,095 B2 | 9/2003 | Kobayashi et al. | |
| 6,662,030 B2 | 12/2003 | Khalil et al. | |
| 6,671,528 B2 | 12/2003 | Steuer et al. | |
| 6,675,029 B2 | 1/2004 | Monfre et al. | |
| 6,687,519 B2 | 2/2004 | Steuer et al. | |
| 6,690,958 B1 | 2/2004 | Walker et al. | |
| 6,701,170 B2 * | 3/2004 | Stetson | 600/323 |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,850,053 B2 | 2/2005 | Daalmans et al. | |
| 6,873,865 B2 | 3/2005 | Steuer et al. | |
| 6,898,451 B2 | 5/2005 | Wuori | |
| 6,949,081 B1 | 9/2005 | Chance | |
| 7,006,676 B1 | 2/2006 | Zeylikovich et al. | |
| 7,010,341 B2 | 3/2006 | Chance | |
| 7,035,697 B1 | 4/2006 | Brown | |
| 7,041,063 B2 | 5/2006 | Abreu | |
| 7,043,289 B2 | 5/2006 | Fine et al. | |
| 7,065,392 B2 | 6/2006 | Kato | |
| 7,095,491 B2 | 8/2006 | Forstner et al. | |
| 7,103,402 B2 | 9/2006 | Vo-Dinh | |
| 7,139,603 B2 | 11/2006 | Chance | |
| 7,187,441 B1 | 3/2007 | Sevick-Muraca et al. | |
| 7,218,959 B2 | 5/2007 | Alfano et al. | |
| 7,236,811 B2 | 6/2007 | Schmitt | |
| 7,239,902 B2 | 7/2007 | Scmitt et al. | |
| 7,268,873 B2 | 9/2007 | Sevick-Muraca et al. | |
| 7,272,426 B2 | 9/2007 | Schmid | |
| 7,349,731 B2 | 3/2008 | Jiang | |
| 7,392,075 B2 * | 6/2008 | Baker, Jr. | 600/336 |
| 7,469,158 B2 | 12/2008 | Cutler et al. | |
| 7,551,950 B2 | 6/2009 | Cheng | |
| 7,621,877 B2 | 11/2009 | Schnall | |
| 8,123,695 B2 * | 2/2012 | Baker, Jr. | 600/323 |
| 2002/0042558 A1 | 4/2002 | Mendelson | |
| 2002/0156354 A1 | 10/2002 | Larson | |
| 2002/0198443 A1 | 12/2002 | Ting | |
| 2003/0009091 A1 | 1/2003 | Edgar | |
| 2003/0023140 A1 | 1/2003 | Chance | |
| 2004/0127779 A1 | 7/2004 | Steuer et al. | |
| 2004/0171920 A1 | 9/2004 | Mannheimer et al. | |
| 2005/0113651 A1 | 5/2005 | Wood et al. | |
| 2005/0113656 A1 | 5/2005 | Chance | |
| 2005/0192488 A1 | 9/2005 | Bryenton et al. | |
| 2005/0228248 A1 | 10/2005 | Dietiker | |
| 2006/0020181 A1 | 1/2006 | Schmitt | |
| 2006/0063995 A1 | 3/2006 | Yodh et al. | |
| 2006/0247501 A1 | 11/2006 | Ali | |
| 2008/0077022 A1 | 3/2008 | Baker | |

FOREIGN PATENT DOCUMENTS

| | | |
|---|---|---|
| EP | 0702931 | 3/1996 |
| EP | 1491135 | 12/2004 |
| JP | 3170866 | 7/1991 |
| JP | 3238813 | 10/1991 |
| JP | 4191642 | 7/1992 |
| JP | 4332536 | 11/1992 |
| JP | 7124138 | 5/1995 |
| JP | 7136150 | 5/1995 |
| JP | 10216115 | 8/1998 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004113353 | 4/2004 |
| JP | 2004135854 | 5/2004 |
| JP | 2004194908 | 7/2004 |
| JP | 2004202190 | 7/2004 |
| JP | 2004248819 | 9/2004 |
| JP | 2004290545 | 10/2004 |
| WO | WO9101678 | 2/1991 |
| WO | WO9221281 | 12/1992 |
| WO | WO9309711 | 5/1993 |
| WO | WO9313706 | 7/1993 |
| WO | WO9403102 | 2/1994 |
| WO | WO9512349 | 5/1995 |
| WO | WO9727801 | 8/1997 |
| WO | WO9749330 | 12/1997 |
| WO | WO9842249 | 10/1998 |
| WO | WO9842251 | 10/1998 |
| WO | WO9843071 | 10/1998 |
| WO | WO9932030 | 7/1999 |
| WO | WO0021438 | 4/2000 |
| WO | WO2005009221 | 2/2005 |

OTHER PUBLICATIONS

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075, 1998.

Hayes, Matthew J., et al.; "Quantitative evaluation of photoplethysmographic artifact reduction for pulse oximetry," *SPIE*, vol. 3570, pp. 138-147 (Sep. 1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Kaestle, S.; "An Algorithm for Reliable Processing of Pulse Oximetry Signals Under strong Noise Conditions," *Dissertation Book*, Lubeck University, Germany (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2000).

Lopez-Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

A. Johansson; "Neural network for photoplethysmographic respiratory rate monitoring," *Medical & Biological Engineering & Computing*, vol. 41, pp. 242-248 (2003).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 2004, pp. 2153-2156.

Matsuzawa, Y., et al.; "Pulse Oximeter," *Home Care Medicine*, pp. 42-45 (Jul. 2004); (Article in Japanese—contains English summary of article).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

R. Neumann, et al.; "Fourier Artifact suppression Technology Provides Reliable $SpO_2$," *Abstracts*, A11, p. S105. (undated).

International Search Report PCT/US2010/047998, 4 pages, mailed Nov. 30, 2010.

\* cited by examiner

METHOD OF ANALYZING PHOTON DENSITY WAVES IN A MEDICAL MONITOR

BACKGROUND

The present disclosure relates generally to a tissue analysis system that utilizes emission and detection of photon density waves to assess tissue characteristics, and, more particularly, to a system for evaluating scattering properties of tissue based on distribution of photons in photon density waves emitted into the tissue and features of the photon density waves detected after passing through the tissue.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Pulse oximetry may be defined as a non-invasive technique that facilitates monitoring of a patient's blood flow characteristics. For example, pulse oximetry may be used to measure blood oxygen saturation of hemoglobin in a patient's arterial blood and/or the patient's heart rate. Specifically, these blood flow characteristic measurements may be acquired using a non-invasive sensor that passes light through a portion of a patient's tissue and photo-electrically senses the light through the tissue. Typical pulse oximetry technology currently utilizes two light emitting diodes (LEDs) that emit different wavelengths of light and a single optical detector to measure the pulse rate through and oxygen saturation of a given tissue bed.

A typical signal resulting from the sensed light may be referred to as a plethysmographic waveform. It should be noted that the amount of arterial blood in the tissue is generally time varying during a cardiac cycle, which is reflected in the shape of plethysmographic waveforms. Such measurements are largely based on absorption of emitted light by specific types of blood constituents and do not specifically take scattering into account. Indeed, traditional pulse oximeters make measurements based on a manipulation of the Lambert-Beer Law, and commonly assume that the two different wavelengths of light from light emitters travel the same path length through the same tissue. Thus, scattering differences are essentially not taken into account. However, once acquired, absorption measurements, as typically acquired by traditional pulse oximeters, may be used with various algorithms to estimate a relative amount of blood constituent in the tissue. For example, such measurements may provide a ratio of oxygenated to deoxygenated hemoglobin in the volume being monitored.

The accuracy of blood flow characteristic estimation via pulse oximetry depends on a number of factors. For example, variations in light absorption characteristics can affect accuracy depending on where the sensor is located and/or the physiology of the patient being monitored. Additionally, various types of noise and interference can create inaccuracies. For example, electrical noise, physiological noise, and other interference can contribute to inaccurate blood flow characteristic estimates. Some sources of noise are consistent, predictable, and/or minimal, while some sources of noise are erratic and cause major interruptions in the accuracy of blood flow characteristic measurements. Accordingly, it is desirable to enable more accurate and/or controlled measurement of physiologic parameters by providing a system and method that takes path length and tissue scattering properties into account, and that addresses inconsistencies in physiologic characteristics of patients and issues relating to noise.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
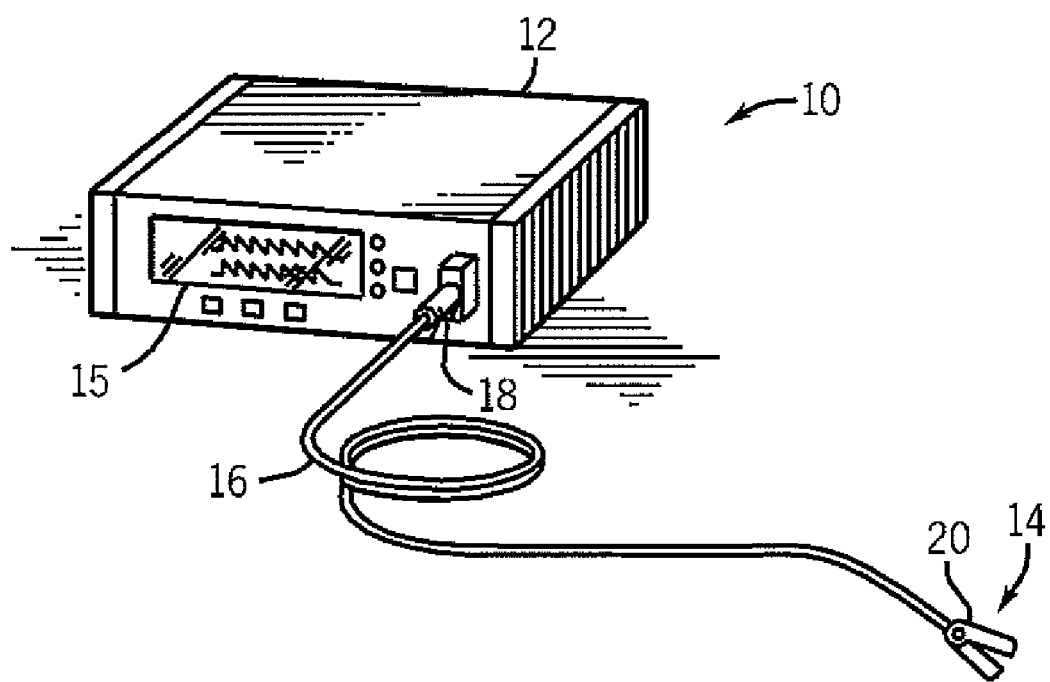
FIG. 1 illustrates a perspective view of a pulse oximeter system capable of utilizing photon density waves in accordance with present embodiments.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiologic parameters corresponding to blood flow in a patient by emitting light into a patient's tissue with light emitters (e.g., lasers/LEDs) and photoelectrically detecting the light after it has passed through the patient's tissue. Indeed, present embodiments are directed to modulating the emitted light at high frequencies to generate resolvable photon density waves that are passed through tissue and detected for analysis of changes in the characteristics of an emitted and detected photon density wave. Generation of the resolvable photon density waves may include essentially turning light sources on and off at a high frequency such that modulation in the 10-1,000 megahertz range is achieved.

Photon density waves may be described as progressively decaying waves of intensity. On a microscopic level, photons generated by an emitter or light source (e.g., a laser diode) generally make random migrations in a scattering medium (e.g., tissue). At a given modulation frequency, the photons collectively form a photon density wave that moves away from the light source. Photon propagation is generally dictated by scattering and absorption in the medium through which the waves are moving. Like other waves, photon density waves undergo refraction, diffraction, interference, dispersion, attenuation, and so forth. In accordance with the present disclosure, the photons of the photon density wave may propagate through the tissue to be detected by a photodetector component of a sensor or monitor. Once the photon density waves have been detected, phase changes and amplitude changes in the photon density waves may be analyzed to facilitate measurement of changes in total scattering particles and absorber concentration, respectively, in the observed medium. Indeed, the phase of such waves may be sensitive to scattering and the amplitude of such waves may be sensitive to absorption.

Further, in accordance with the present disclosure, the distribution of detected photons from a resolvable photon density wave may be detected and analyzed after passing through the patient's tissue. More specifically, a photon density wave signal (PDW signal) may be generated by a light detection feature in response to detecting light from a photon density wave after it has passed through the observed tissue. The PDW signal may be indicative of a distribution of detected photons over time. Once, acquired, the PDW signal may be analyzed to facilitate identification and/or measurement of certain characteristics of the tissue being monitored. Indeed, the PDW signal may contain phase and amplitude information for the photon density waves that are transmitted via the patient's tissue from the light emitters to the detector, and this wave information may correlate to certain physiological characteristics of the tissue being observed. Specifically, the PDW signal may be used to quantify the time-delay or phase-delay between the modulation waveform (e.g., a square wave) applied to the light emitter and the waveform of the light after being passed through the tissue.

Specifically, certain features of the detected photon density waves may be measured and compared to empirical data to provide information about the tissue through which the photon density waves passed, such as the nature of the vasculature within the tissue, the hemoglobin flowing through the tissue, and potential disease conditions of the tissue. Indeed, with regard to the detection of photon density wave features, the present disclosure is directed to evaluating a time-delay and/or phase-delay of photon density waves, and, thus, scattering properties, by analyzing higher moments of the detected light signals. For example, the asymmetry of a series of decay waveforms may be quantified by computing the skewness (third moment) of the derivative of the modulated detected waveform. The signal-to-noise level of the derivative of the modulated detected waveform or PDW signal may be enhanced using ensemble averaging, triggered by the modulation waveform being applied to the emitter. Further, an input-triggered ensemble averaging technique may be used with a non-repeating input modulation pattern, which would be relatively immune to fixed external interference frequencies. In accordance with present embodiments, evaluating a PDW signal using such techniques may facilitate identification of issues relating to blood flow (e.g., structural conditions of tissue) based on detection of signal characteristics, such as those signal characteristics that are indicative of rapid filling of the observed tissue with hemoglobin.

FIG. 1 illustrates a perspective view of a pulse oximetry system 10 in accordance with some embodiments. The system 10 includes a pulse oximeter or monitor 12 that communicatively couples to a sensor 14. The monitor 12 may include a display 15, a memory, a processor, and various monitoring and control features. The sensor 14 may include a sensor cable 16, a connector plug 18, and a sensor assembly or body 20 configured to attach to a patient (e.g., a patient's finger, ear, lip, or toe) in a manner that facilitates passage of light through the patient's tissue in reflectance and/or transmission mode. The system 10 may be utilized to observe the blood constituents of a patient's arterial blood to facilitate estimation of the state of oxygen exchange in the patient's body by emitting waves into tissue and detecting the waves after dispersion and/or reflection by the tissue. The amount of light that passes through the tissue and other characteristics of light waves may vary in accordance with the changing amount of certain blood constituents in the tissue and the related light absorption and/or scattering. For example, as with conventional pulse oximeter systems, the system 10 may emit light from two or more LEDs or lasers (e.g., laser diodes) into pulsatile tissue and then detect the transmitted light with a light detector (e.g., a photodiode or photo-detector) after the light has passed through the pulsatile tissue. Such measurements may be utilized to estimate a percentage of blood oxygen saturation in the probed volume of blood. Additionally, in accordance with present embodiments, the system 10 may modulate the emitted light to generate photon density waves at a high frequency such that phase shifts may be detected that correlate predominantly to scattering particles in the probed volume of blood and tissue.

Changes in phase of a photon density wave signal may correspond to a total number of scattering and absorbing particles, such as total hemoglobin contained in red blood cells, observed in the medium (e.g., tissue). For example, since the scattering coefficient of the tissue may change depending on the total number of scattering particles in the tissue, variations in the phase changes may correspond to variations in the total hemoglobin in the tissue. Thus, changes in the phase of a photon density wave signal may be predominately due to the total number of scattering particles (i.e., total hemoglobin), rather than to the ratio of different types of absorbers (e.g., oxygenated and deoxygenated hemoglobin) in the tissue. Detection of phase changes in the photon density waves generated by modulation at high frequency may correspond to a total number of scattering particles because the wavelength of the photon density waves may be shorter than an average absorption length of photons, thus, making a resolvable correlation between phase shift and scattering particles. Accordingly, detected variations in the phase may be predominantly due to the scattering coefficient and not absorption. In other words, the variation in phase may be predominantly due to the total number of scattering particles (e.g., total red blood cells containing hemoglobin) in the observed medium and not merely a ratio of absorbers (e.g., oxygenated and deoxygenated hemoglobin) that absorb different colors of light.

It should be noted that, inasmuch as the changes in phase correspond to a total number of scattering particles, the phase changes also correspond to the path length traversed by the photons of the photon density wave through the tissue. Thus, instead of assuming a path length, as in traditional pulse oximetry techniques, present embodiments provide an empirical indication of path length. Indeed, it is now recognized that the assumption in traditional pulse oximetry that differences in path lengths for different light sources (e.g., red and infrared) are solely a function of saturation may be a source of inaccuracy. For example, different path length ratios between the different wavelengths of light may be due to a number of variables, such as a change in blood volume, finger size, spacing between the emitter and detector, pressure, and pigmentation. Accordingly, present embodiments are directed to calculation of a mean path length, which may represent the distance traveled by the photons of a photon density wave, including deflections in different directions due to scattering. Indeed, in accordance with present embodiments, path length may essentially be calculated by multiplying the time interval corresponding to a detected phase delay by the speed of light in the observed medium (e.g., a patient's tissue). Once acquired, calculated and empirically determined values for optical monitoring path lengths in tissue, and variations therein, may be utilized to evaluate tissue scattering properties, and thereby enhance the accuracy of determinations of blood and/or tissue analytes.

While present embodiments facilitate determining a quantity of scattering particles and path length traversed by emitted photons, present embodiments may still be utilized to determine absorption characteristics as well. Indeed, changes in the amplitude of the photon density waves may correspond to absorption of specific light colors (e.g. red or infrared light) in the observed volume, and, thus, a ratio of different types of particles (e.g., oxygenated and deoxygenated hemoglobin) in the observed medium. For example, red blood cells containing oxygenated and deoxygenated hemoglobin molecules may scatter the photons of the modulated photon density waves, but may also absorb different frequencies of light. Thus, by analyzing the changes in amplitude in the photon density wave signal, a ratio of different types of absorbers in the tissue may be estimated. Accordingly, using photon density waves may facilitate measurement or estimation of a total number of particles in a medium, a general path length value for photons passing through the medium, and a ratio of types of constituents within the medium (e.g., oxygenated and deoxygenated hemoglobin). In other words, data acquired using photon density waves may provide additional physiological information to that which is typically provided by pulse oximetry techniques.

As generally indicated above, the system 10 may generate and detect light waves to facilitate non-invasive measurement of a patient's physiological characteristics. The system 10 may generate resolvable photon density waves and make relative measurements of certain detected wave characteristics after the waves have been transmitted from one side of a medium (e.g., the tissue of a patient's finger) to the other, or reflected such that light passes through the medium from one side and returns to a different location on the same side. Specifically, as set forth above, the detected light may be converted into a PDW signal that is representative of a distribution of photons detected over time, and this signal may be analyzed to identify wave characteristics. The wave characteristics that may be measured in accordance with present embodiments may include characteristics that relate predominantly to absorption of the emitted light in the observed medium (e.g., amplitude change) and characteristics that relate predominantly to scattering in the observed medium (e.g., phase shift). Specifically, skewness of the PDW signal may be evaluated in accordance with the present disclosure. It should be noted that, as will be discussed further below, the correlation of certain wave characteristic (e.g., amplitude and phase) measurements to certain medium characteristics (e.g., quantity of scattering particles, path length, and blood oxygen saturation) may be based on high frequency modulation of the system's light sources, which generate the resolvable photon density waves.

Further, the system 10 may include an analysis feature (e.g., a programmed memory and processor of the monitor 12) that is programmed to quantify the time-delay and/or phase-delay between the modulation waveform applied to the light emitter and the modulation of the light detected after being scattered through the tissue. Specifically, such an analysis feature may be programmed to perform this quantification based on an evaluation of the skewness of a data distribution acquired by recording characteristics of a photon density wave that is emitted and detecting characteristics of the photon density wave after passing through the observed tissue. This may be achieved by coordination of the monitor 12 and the sensor 14. Specifically, the skewness of measured photon density wave distributions may be compared with empirical data or the like to identify correlations between the observed tissue and certain tissue conditions and so forth. Specific features relating to determining skewness will be discussed in detail below.

Skewness may be described as a characterization of a degree to which a distribution is asymmetrical about its mean. A distribution may be considered asymmetrical when its median, mean, and mode are not equal. Further, there are generally two types of skewness. Indeed, a distribution may be considered positively skewed when the mean exceeds the median, and a distribution may be considered negatively skewed when the mean is less than the median. These conditions (i.e., positively skewed and negatively skewed) may also be referred to as being skewed to the right and skewed to the left, respectively.

More specifically, skewness is the third standardized moment about the mean and may be calculated using the following equation:

$$\text{Skewness} = \frac{\sum (y_i - \bar{y})^3}{(n-1)s^3};$$

where $y_i$ represents the photon detection value for each point of the distribution, $\bar{y}$ represents an average value for the points of the distribution, n represents the total number of points in the distribution, and s represents the standard deviation. That is, skewness may be calculated by summing the deviations of the values of the distribution from a mean of the distribution, raising the sum to the third power, and then dividing by the product of the standard deviation raised to the third power and the value of one less than the number of cases. Specifically, in accordance with present embodiments, the asymmetry of a series of decay waveforms may be quantified by computing the skewness of the derivative of the PDW signal, which is obtained from a modulated detected waveform. The signal-to-noise level of the derivative of the PDW signal, and any skewness metric computed therefrom, may be enhanced using ensemble averaging, triggered by the modulation waveform being applied to the emitter. In accordance with the present disclosure, this input-triggered ensemble-averaging technique may be used with a non-repeating input modulation pattern, which would be relatively immune to fixed external interference frequencies. With regard to the obtained value for a positive skewness, it should be noted that, in some embodiments, the further the calculated value for skewness gets from zero, the more it is illustrative of lagging photons and scattering. The skewness may also be indicative of the structure of vasculature and so forth. For example, certain skewness values may be indicative of large blood vessels in the tissue that receive large amounts of hemoglobin in a short amount of time, or constricted vessels that are unable to receive a large amount of hemoglobin. The values for skewness may be compared to empirical data to ascertain tissue characteristics such as these and others. Indeed, the skewness may be compared to empirical data to identify potential disease conditions of the tissue and/or hemoglobin.

In accordance with the present disclosure, a distribution of photons detected from a photon density wave over time will generally have a positive skew because a majority of the photons in the photon density wave will be detected at approximately the same time with the remaining photons being detected in progressively lower amounts. This trailing off of detected photons may occur because most of the photons will have taken paths of similar length through the observed tissue, while progressively fewer take relatively longer and longer paths due to scattering. That is, there will typically be fewer lagging photons that have been dispersed by scattering particles to take longer paths, thus, producing a distribution that is skewed right.

Figure 2A:
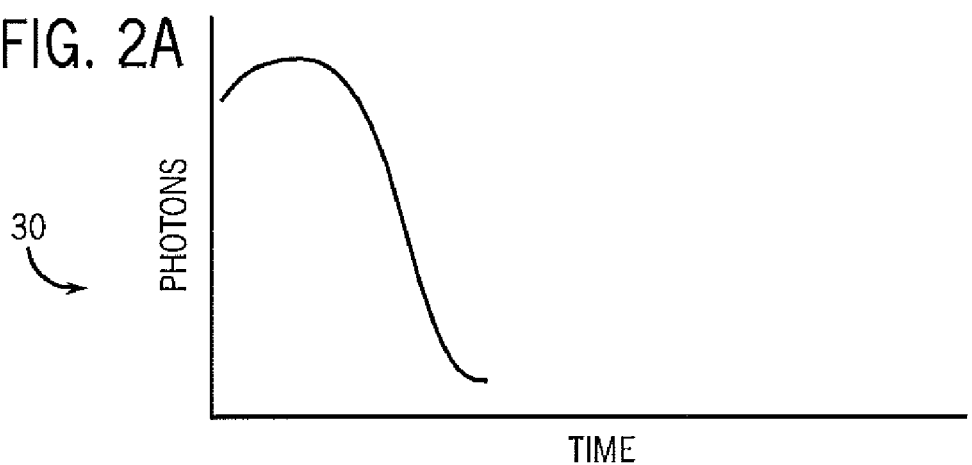
FIG. 2 illustrates a set of graphs that are representative of skewness in three different photon density wave signals in accordance with present embodiments.
Figure 2B:
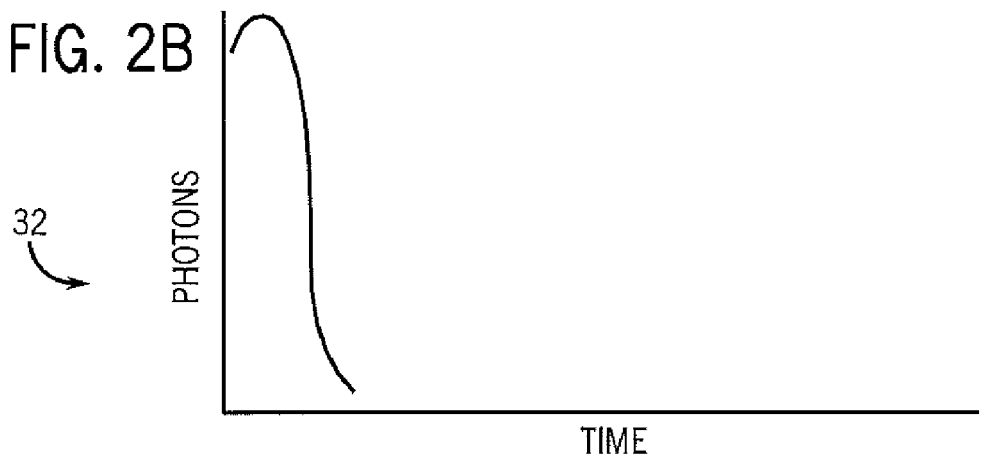
Figure 2C:
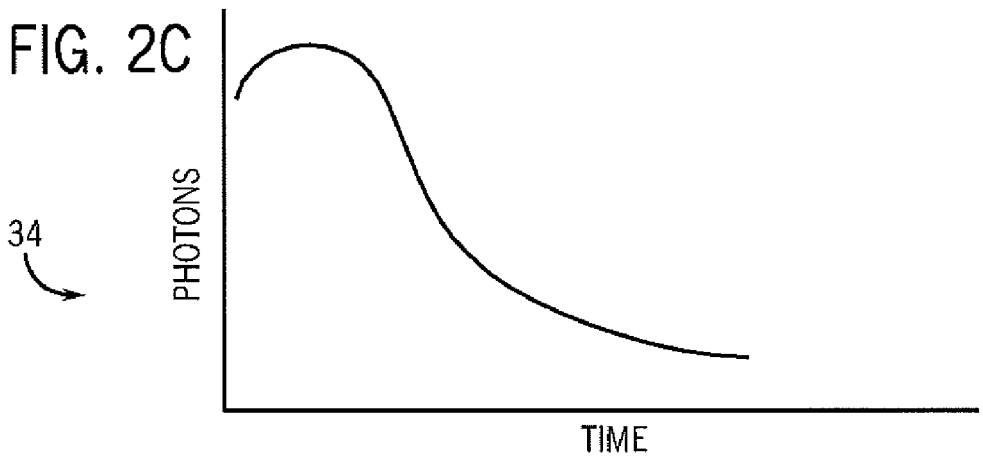

FIG. 2 includes representative graphs of skewness for several different types of PDW signals, which each correspond to different distributions of detected photons over time. Specifically, FIG. 2 illustrates three graphs, a first graph 30 in FIG. 2A, a second graph 32 in FIG. 2B, and a third graph 34 in FIG. 2C, which each represent detected photons on the Y-Axis and time on the X-Axis. Each of the graphs 30, 32, and 34 represent a different scenario of photon detection decay. In each scenario, the skewness of the depicted distribution is positive. However, in the first graph 30 and the second graph 32, a rapid decay in photon detection is represented, and, in the third graph 34, a gradual decay in photon detection is represented. A rapid decay, as illustrated in the first graph 30 may be indicative of very few scattering particles in the observed tissue. Because there are few scattering particles, almost all of the photons may be detected at approximately the same time and very few photons may be scattered along a longer path length such that they are detected later. An even more rapid decay, as illustrated by the exponential decay in the second graph 32, may be indicative of shunting. Indeed, when there is shunting, almost all of the photons may follow the same, essentially straight path from the emitter to the detector. A slower decay, as represented by the third graph 34, is generally indicative of more scattering and photons going farther along paths within the tissue from the emitter to the detector. This would be indicative of tissue having more scattering particles therein.

Figure 3:
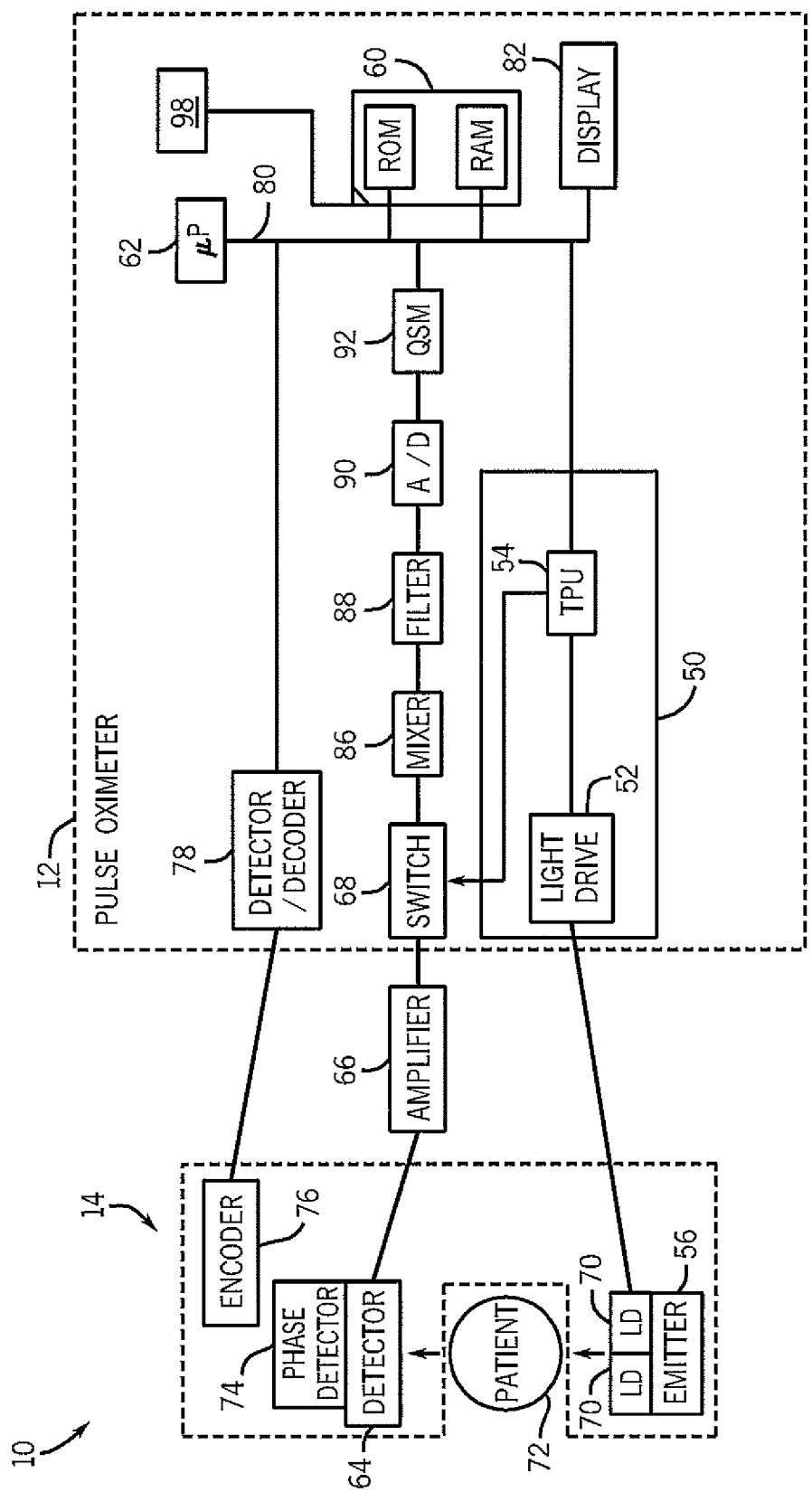
FIG. 3 illustrates a block diagram of a pulse oximeter system capable of utilizing photon density waves in accordance with present embodiments.

FIG. 3 is a basic block diagram of an embodiment of the pulse oximeter system 10 that is capable of photon density wave emission and detection. As in FIG. 1, the system 10 illustrated in FIG. 3 includes the monitor 12 and the sensor 14. The sensor 14, in the illustrated embodiment, is configured for transmission mode operation, which may enable deep penetration of the photon density waves into a region of interest in a patient's tissue. However, in other embodiments, the sensor 14 may be configured for reflectance mode operation. It should be noted that in some embodiments, multiple sensors may be employed. Further, in some embodiments, one or more sensors may each include multiple emitters and/or detectors. If multiple emitters are employed, it will generally be desirable for each of the emitters to include red and infrared (IR) light sources.

The monitor 12 is illustrated as including various functional components that facilitate emission, detection, and analysis of photon density waves. For example, in the illustrated embodiment, the monitor 12 includes a modulator 50, which includes a light driver 52 and a time processing unit (TPU) 54 that cooperate to modulate the light emissions of an emitter 56 disposed in the sensor 14 at a high frequency to generate photon density waves. The modulator 50 may include a hardware feature, a software feature, or some combination thereof. For example, a portion of the modulator 50 may be stored on a memory 60 and may be controlled by a processor 62. As indicated above, in the illustrated embodiment, the modulator 50 includes the light driver 52 and the TPU 54 that cooperate to modulate the light emitter 56. The TPU 54, which may include a sine wave or square wave generator, may provide timing control signals to the light drive circuitry 52, which controls when the emitter 56 is activated, and if multiple light sources are used, the multiplexed timing for the different light sources. The TPU 54 may also control the gating-in of signals from a detector 64 through an amplifier 66 and a switching circuit 68. These signals may be sampled at the proper time, depending at least in part upon which of multiple light sources is activated, if multiple light sources are used.

Figure 4:
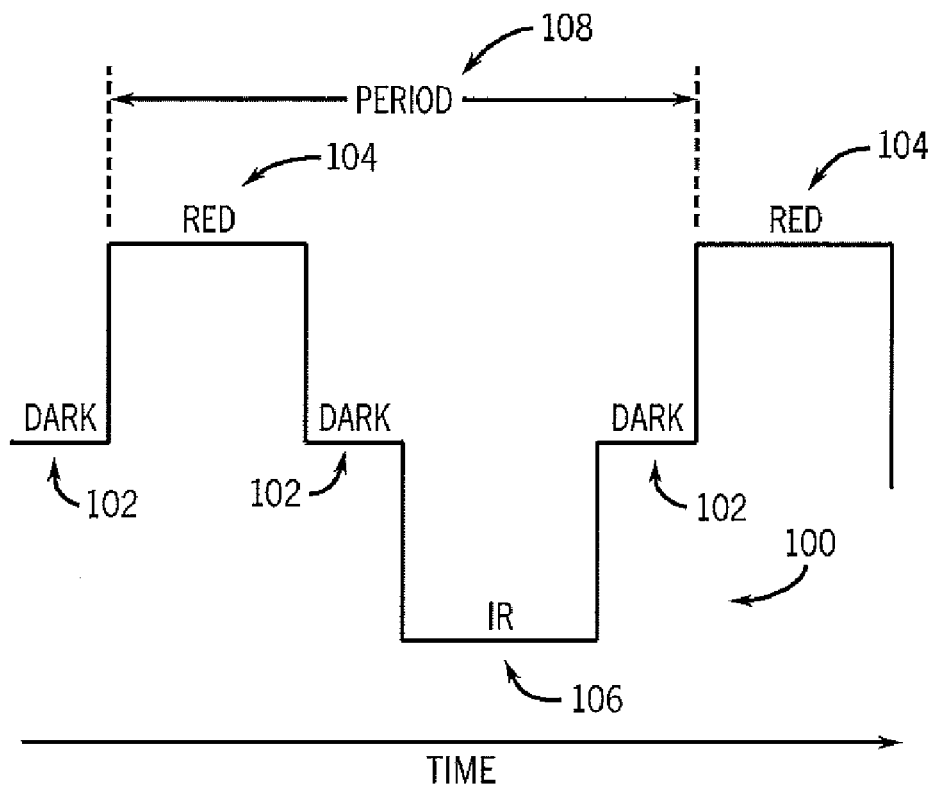
FIG. 4 illustrates an example of a source modulation signal in accordance with present embodiments.

FIG. 4 illustrates an example of a source modulation signal as driven by cross-coupled light emitters (e.g., LEDs or lasers) in accordance with some embodiments. Specifically, FIG. 4 illustrates a control signal 100 that may be generated by the modulator 50 to activate and/or deactivate the emitter 56 including red and IR light sources, such as a pair of laser diodes (LDs) 70, as illustrated in FIG. 3. In other embodiments, separate modulators may be utilized for each light source and/or additional light sources. Indeed, when multiple emitters are utilized, each emitter may be modulated by a separate modulator.

In the illustrated embodiment, the control signal 100 is representative of dark intervals 102, intervals of power 104 being supplied to a red LD, and intervals of power 106 being supplied to an IR LD over time. Further, the control signal 100 has a period designated by reference number 108. This period 108 may be adjusted such that each of the LDs 70 may be modulated with a desired frequency (e.g., 50 MHz to 3.0 GHz) to generate photon density waves. Such adjustments to the modulation frequency may facilitate detection of phase shifts in the photon density waves, and, thus, variations in scattering based on such phase shifts. As may be appreciated by those of ordinary skill in the art, the control signal 100 may be adjusted or modified for different scenarios. For example, the control signal 100 may be adjusted to be generally sinusoidal, adjusted to include various intensity levels, and so forth. The sinusoidal nature of the wave may be controlled by a wave generator and the intensity levels may be adjusted by providing more power and/or by reducing dark intervals and increasing the length of time that light is emitted.

Turning specifically to the features of the sensor 14 in the illustrated embodiment, it should be noted that, while other light emission features may be utilized, the emitter 56 includes the pair of LDs 70. As discussed above, the emitter 56 may receive modulated drive signals from the monitor 12 that activate the LDs 70 and cause them to emit light at certain intervals. Thus, the monitor 12 may activate and deactivate the LDs 70 at high frequencies that may facilitate measurements relating to scattering in the probed medium based on phase changes in emitted photon density waves. These resolvable photon density waves may then be transmitted by the emitter 56 into tissue 72. It should be noted that, in some embodiments, the emitter 56 may be positioned in the pulse oximeter 12 and the photon density waves may be transmitted to the sensor 14 and the tissue 72 via fiber optic cable. Indeed, fiber optic cable may be utilized for communication of emitted and received light between the sensor 14 and the monitor 12 to reduce the cost of the sensor 14 by limiting the number of functional components disposed therein.

The photon density waves may pass through the tissue 72 to be detected by the photodector 64, which, as with the emitter 56, may be positioned in the monitor 12 in some embodiments. Once the light is received by the photo-detector 64, whether via transmission or reflectance, the photo-detector 64 may then convert the received light into a photocurrent signal or PDW signal. The photo-detector 64 may include or utilize a signal processing device capable of providing photon distribution data by determining a derivative of a detected waveform of the photon density waves. The photo-detector 64 may also include a noise-reduction feature capable of enhancing a single-to-noise level of the distribution of detected photons using an ensemble averaging procedure. Indeed, the noise-reduction feature may be capable of triggering the ensemble averaging procedure based at least in part on a modulation waveform produced by the modulator to modulate the emitter. In some embodiments, this noise-reduction feature may be separate from the photo-detector 64. Regardless, once the PDW signal is obtained, it may then be provided to the monitor 12 and/or other sensor components for analysis. For example, the sensor 14 and/or the monitor 12 may also include a phase detector 74 capable of analyzing the PDW signal and detecting phase shifts in photon density waves observed by the detector 64. While the phase detection feature 74 is positioned within the sensor 14 in the illustrated embodiment, in some embodiments, the phase detection feature 74 may be located within the oximeter 12. Additionally, the sensor 14 may include an encoder 76 (e.g., a resistor or chip) which may be capable of providing signals indicative of the wavelength(s) of light received from the emitter 56 to allow the oximeter 12 to select appropriate calibration coefficients for calculating oxygen saturation. The data or signal from the encoder 76 may be decoded by a detector/decoder feature 78 in the oximeter 12.

In some embodiments, functional features of the monitor 12, such as the microprocessor 62, may be coupled to an internal bus 80 of the monitor 12. For example, the bus 80 may communicatively couple the microprocessor 62, the memory 60 (e.g., RAM and/or ROM) and a display 82. Further, the bus 80 may communicatively couple the switch 68, a mixer (analog multiplier) 86, a filter 88, an analog-to-digital converter 90, and a queued serial module (QSM) 92. During operation of the system 10, received signals from the detector 64 may be passed through the amplifier 66, the switch 68, the analog multiplier 86, the low pass filter 88, and/or the analog-to-digital converter 90. The digital data may then be stored in the QSM 92 for later downloading to the memory 60 as the QSM 92 fills up. In some embodiments, there may be multiple parallel paths of separate amplifier, filter, and A/D converters for multiple light wavelengths or spectra received, and/or for phase data generated by the phase detector 74. In one embodiment, a signal from the phase detector 74 may be processed in any suitable manner, and may be sent through a different data path than the signal from the detector 64, which may be configured to detect amplitude of the photon density waves. The received optical signal may be converted into an electrical signal at the detector 64. The electrical signal may then be amplified by the amplifier 66 and sent to a frequency mixer or analog multiplier (e.g., mixer 86) to generate a signal that is proportional to a phase difference between a reference oscillator (not shown) and the received signal. Similarly, the AC and DC amplitudes of the received signal may be determined with peak detection circuits and low pass filters (e.g., filter 88).

As indicated above, when the system 10 is being utilized to monitor living tissue, the amplitude of the PDW signal from the detector 64 generally drops over time based on reduced detection of photons over time due to scattering. Indeed, a relative number of photons detected within a narrow window of time is generally very high and then falls off due to the substantial scattering of a subset of the photons generated as part of the photon density wave. The rate of decay may vary depending on the tissue characteristics (e.g., hemoglobin content). Accordingly, a rate of decay of the detected photon density waves may be detected and analyzed by the system 10 by programming the system 10 to observe a skewness of the PDW signal. Indeed, the skewness of detected photons can be an empirical indicator of path length distribution, which may be described as a distribution of the distance traveled by each of the photons in a photon density wave through the observed tissue. It should be noted that the path length for a particular photon includes distances traveled in different directions, as caused by scattering.

Accordingly, in some embodiments, the monitor 12 may include a signal analysis module 98 that is configured to analyze the PDW signal from the detector 64 or another component to determine skewness of the data acquired from detection of the photon density wave after passing through the tissue 72. For example, the signal analysis module 98 may include software stored on the memory 60 and/or a hardware feature configured to measure, analyze and compare the skewness of a detected photon density wave with various sets of empircal data or predefined templates to facilitate identification of certain tissue characteristics. While the signal analysis module 98 in the illustrated embodiment is configured to receive a modified signal, in some embodiments, it may receive the PDW signal directly from the detector 64. More specifically, the signal analysis module 98 may be configured or programmed to evaluate a time-delay and/or phase-delay of photon density waves, and, thus, scattering properties, by computing the skewness of the derivative of the modulated detected waveform. Additionally, the signal analysis module 98 may be capable of enhancing the PDW signal using ensemble averaging, triggered by the modulation waveform being applied to the emitter. Further, the signal analysis module 98 may be capable of comparing the PDW signal data with empirical data stored in the memory 60 to facilitate identification of certain tissue conditions and so forth.

As indicated above, the system 10 may be utilized to make measurements that relate predominantly to scattering in the observed volume including and in addition to measurements relating to the eventual calculation of skewness. More specifically, the system 10 may be utilized to make measurements relating to a total amount of scattering particles in the observed volume based on phase shifts detected in the emitted light waves. For example, the system 10 may emit light that is modulated at a high frequency (e.g., 50 MHz to 3.0 GHz) to generate resolvable photon density waves, and then measure the phase shift of these high frequency waves to facilitate estimation of a total number of scattering particles in the observed medium. Similarly, as set forth above, the system 10 may be utilized to make measurements that relate predominantly to absorption in an observed volume. For example, the system 10 may detect changes in AC and DC amplitudes of the resolvable photon density waves to facilitate detection of a ratio of certain constituents in the blood (e.g., a ratio of oxygenated hemoglobin to total hemoglobin). It should be noted that the amplitude changes and phase shifts measured at a detection point may be considered relative to one or more points. For example, the amplitude and phase shifts measured at a detector may be considered relative to the associated values generated at the emitter.

In contrast to traditional pulse oximetry, which conducts measurements at sufficiently low frequencies (e.g., 1.5 KHz) to be considered DC, the modulator 50 may be configured to modulate the LDs 70 at sufficiently high frequencies (e.g., approximately 50 MHz to 3.0 GHz) to cause resolvable photon density waves to propagate through the tissue 72. In some embodiments, the modulator 50 may be configured to sweep a range from 50 MHz to 3.0 GHz. In some embodiments, the modulator 50 may be configured to modulate between 100 MHz and 1 GHz or to sweep a range from 100 MHz to 1 GHz. Thus, present embodiments operate at much higher frequencies than the traditional pulse oximetry sampling frequency of 1 sample every 67 microseconds.

In some embodiments, for continuous modulation of the LDs 70, resolvable amplitude and phase relationships of the photon density waves may be established at various positions from the emitter along the tissue bed 72. By modulating the light emitters at sufficiently high frequencies, the wavelengths of photon density waves may be shorter than the average distance required for light to be absorbed. Thus, the phase changes in the photon density waves can be attributed predominantly to scattering and not absorption. Further, in view of this, it can be determined that detected phase changes correspond to a number of scattering particles or volume change in the probed medium. The frequency of the photon density waves is essentially locked to the initial light source input and the phase change is essentially locked to arterial pulsation and the introduction of scattering particles. Indeed, the variation in AC scattering to DC scattering measured by phase offset may yield information about the total arteriole volume probed.

For a modulation frequency where the product of the frequency and the mean time between absorption events is much larger than 1, the change in phase between two points located a distance r from each other on a tissue bed may be given by the relation, $$\Delta\phi = r\sqrt{\frac{\omega\mu'_s}{6c}},$$

where c is the speed of light, $\omega$ is the angular frequency of modulation, and $\mu'_s$ is the reduced scattering coefficient. The reduced scattering coefficient for a tissue bed is comprised of both blood and surrounding tissue components. It can be written as, $$\mu'_s\text{total} = V_{blood}\mu'_s\text{blood} + V_{tissue}\mu'_s\text{tissue}.$$

The time varying component of this equation at a single wavelength will generally be only the portion due to arterial blood. The time varying component of this equation at a second wavelength will allow for the deconvolution of the scattering coefficient. The scattering coefficient for blood is related to the hematocrit (HCT) through the relation, $$\mu'_s\text{blood} = \sigma_s(1-g)(\text{HCT}/V_i)(1-\text{HCT})(1.4-\text{HCT}),$$

where g is the anisotropy factor, $\sigma$ is the scattering cross section of an erythrocyte, Vi is the volume of an erythrocyte and HCT is the hematocrit.

Accordingly, when the modulator 50 operates at a high enough frequency, measured phase changes in the photon density waves may be utilized to calculate a number of scattering particles in the observed volume. For example, the monitor 12 may be configured to receive phase shift and/or amplitude data from the sensor 14 and calculate a value related to a quantity of scattering particles in the probed tissue for presentation on the display 82. Specifically, the monitor 12 may include instructions or an algorithm stored on the memory 60 and configured to perform such calculations.

Figure 5A:
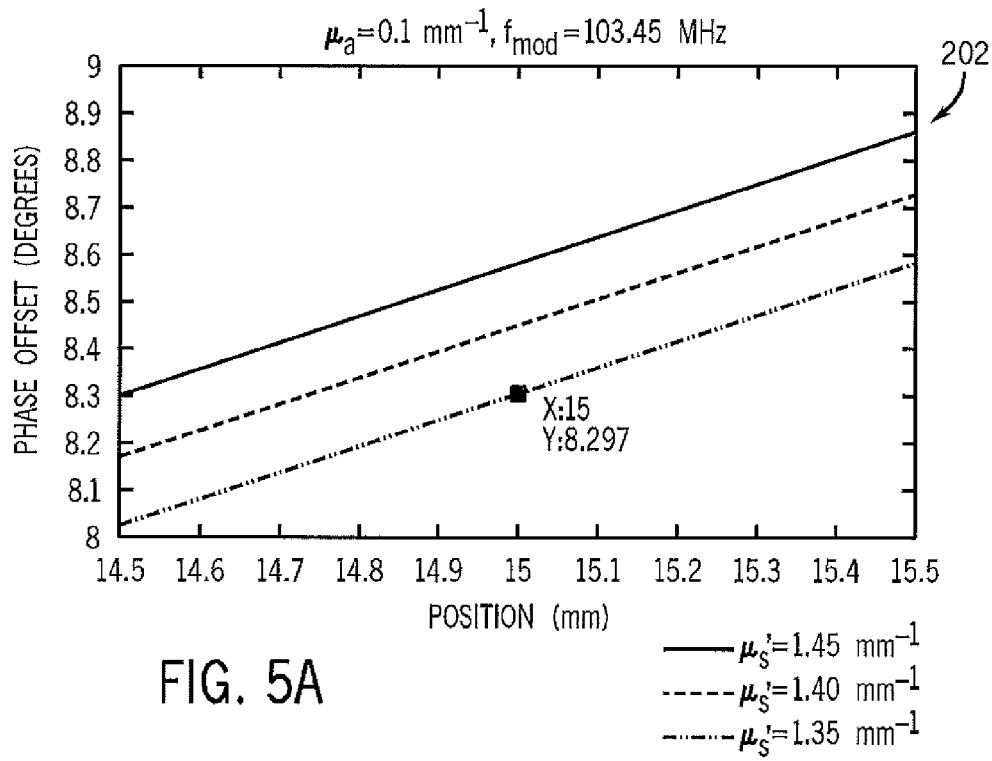
FIG. 5 illustrates a pair of graphs that represent simulations of phase changes in photon density waves modulated at high frequency, wherein the phase changes are due to scattering in accordance with present embodiments.
Figure 5B:
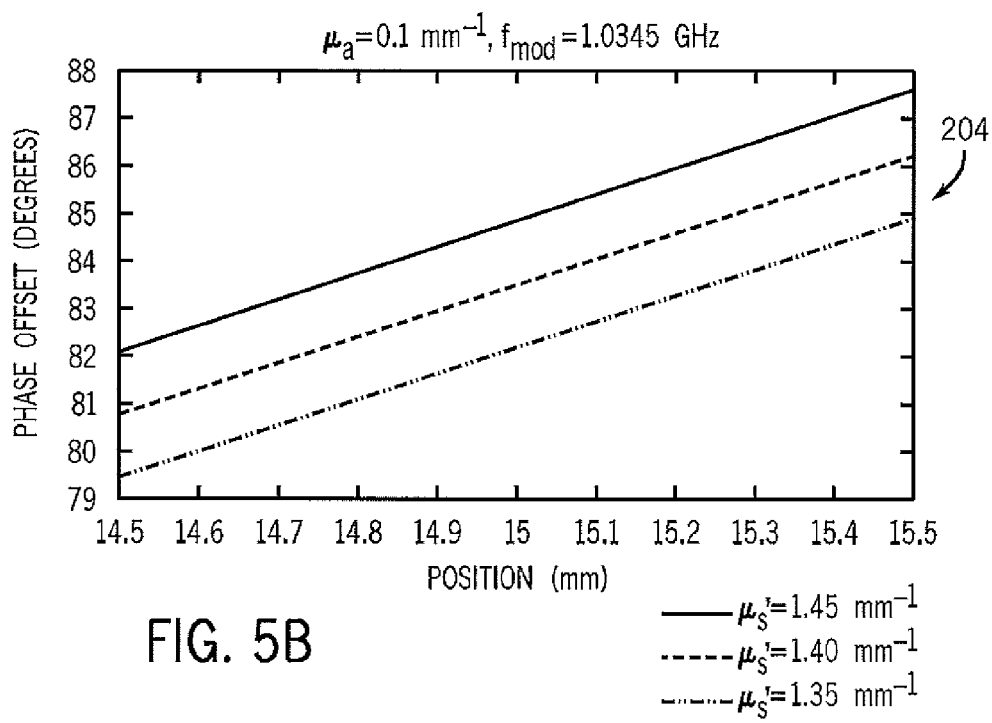

As an example of the correlation of phase change measurements of photon density waves modulated at high frequency to a number of scattering particles in the probed medium, FIGS. 5A and 5B include a pair of graphs that represent simulations of phase changes due to scattering at two different frequencies. Specifically, FIG. 5A includes a first graph 202 and FIG. 5B includes a second graph 204 that each represent simulations of phase change (measured in degrees) due to scattering variation of an arterial pulse (Hemoglobin 15 g/dL) for photon density waves at 890 nm that are modulated with a frequency of 103.4 MHz and 1,034 GHz, respectively. It should be noted that the increase in frequency from 103.4 MHz in the first graph 202 to 1.034 GHz in the second graph 204 results in a phase change of approximately 71-73 degrees. This change correlates to the wavelengths of the photon density waves. In some embodiments, a range of frequencies between those shown in FIGS. 5A and 5B may be swept through to profile the characteristics of the tissue at different photon density wave frequencies.

Scattering may be quantified based on phase change. Specifically, as set forth above, a modulation frequency where the product of the frequency and the mean time between absorption events is much larger than 1, the change in phase between two points may be given by the relation, $$\Delta\phi = r\sqrt{\frac{\omega\mu'_s}{6c}}.$$

Changes in phase due to arterial pulsation may be directly related to the change in scattering coefficient of the medium which is due to the change in the concentration of the number of erythrocytes. It should be noted that a second method for correlating the scattering changes from the phase could involve a calibration curve determined from tissue phantoms or clinical data.

As indicated above, the phase of the photon density waves may be sensitive to changes in the scattering coefficient, while the amplitude of the photon density waves may be sensitive to the concentration of absorbers in the medium. Specifically, with regard to amplitude measurements, the AC amplitude and DC amplitude may yield information about absorption in the volume. Thus, detection of amplitude changes in the photon density waves may be utilized to calculate absorber concentration values in the observed medium, such as blood oxygen saturation values. Such calculations may be made using the standard ratio of ratios (i.e., ratrat) technique for the constant and modulated values of the photon density wave amplitudes at two wavelengths. Once the ratio of ratios values is obtained, it may be mapped to the saturation from clinical calibration curves.

With regard to phase shift measurements, when the wavelengths of the photon density waves get below that of the mean absorption distance, the phase becomes almost exclusively a function of the scattering coefficient. While dependent upon the tissue bed being probed, this is generally believed to occur at a modulation frequency in the range of approximately 500 MHz. Thus, the phase shift measurement may yield information about the number of erythrocytes or red blood cells in the local probed volume. The HCT discussed above is proportional to the number of erythrocytes. Accordingly, by sweeping frequencies, a multi-parameter output may be obtained that relates to standard pulse oximetry measurements as well as the blood hematocrit.

The amplitude and phase at a given frequency may be proportional to the scattering and absorption coefficient at a given wavelength until the product of the frequency and the mean time between absorption events is much larger than 1. When the product of the frequency and the mean time between absorption events is much larger than 1, the amplitude is a function of the absorption and phase is only a function of the scattering. Thus, a frequency sweep may be used to reduce the error in the determination of a single value of reduced scattering coefficient for the blood and a single value of absorption coefficient. Indeed, in some embodiments, the amplitude and phase information may be utilized together to yield a value of total hemoglobin per unit volume.

In some embodiments, by modulating the light sources at a sufficient frequency, and, thus, facilitating a detectable phase shift that corresponds to scattering particles, present embodiments may provide an extra degree of certainty for blood flow parameter measurements. Indeed, the detected amplitude for the photon density waves may be utilized to calculate traditional pulse oximetry information and the phase may be utilized to confirm that such values are correct (e.g., within a certain range of error). For example, the amplitude information may be utilized to calculate a blood oxygen saturation ($SpO_2$) value and empirical data may indicate that a particular $SpO_2$ value should correspond to a particular phase variation at a given frequency. In other words, there may be a certain phase change that should accompany a given increase in absorber observed as a change in amplitude. Various algorithms (e.g., learning based algorithms such as support vector machines, cluster analysis, neural networks, and PCA) based on the measured phase shift and amplitude change may be compared to determine if the amplitude shift and phase shift correlate to a known $SpO_2$. If both the measured amplitude shift and phase shift correlate to a known $SpO_2$, the measured $SpO_2$ value may be deemed appropriate and displayed or utilized as a correct $SpO_2$ value. Alternatively, if the measured amplitude shift and phase shift do not agree, the calculated $SpO_2$ value may be identified as being corrupt or including too much noise and, thus, be discarded.

Figure 6:
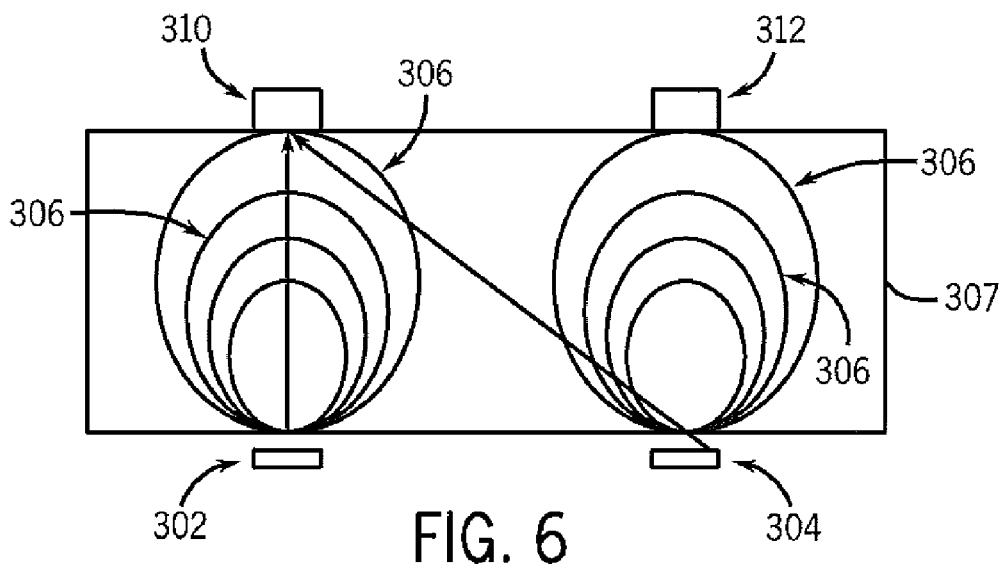
FIGS. 6-8 include representative diagrams of multiple emitter and/or detector arrangements being utilized in conjunction with one another in accordance with present embodiments.
Figure 7:
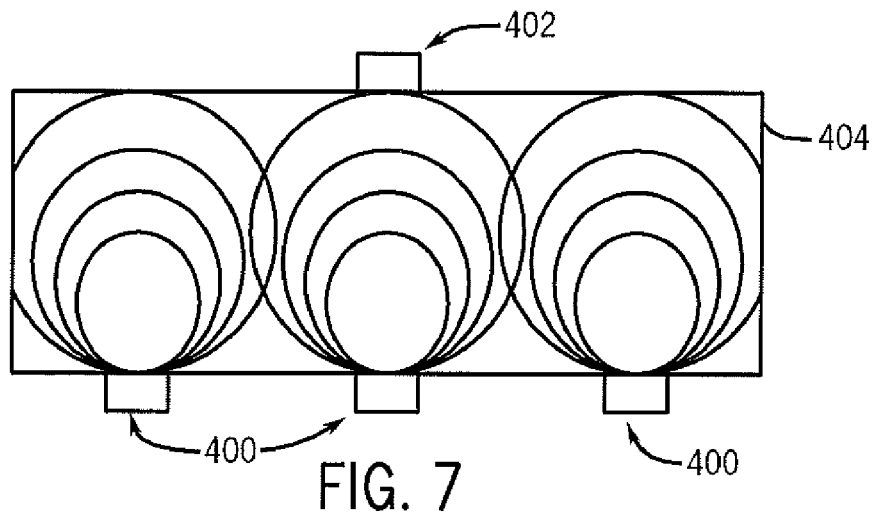
Figure 8:
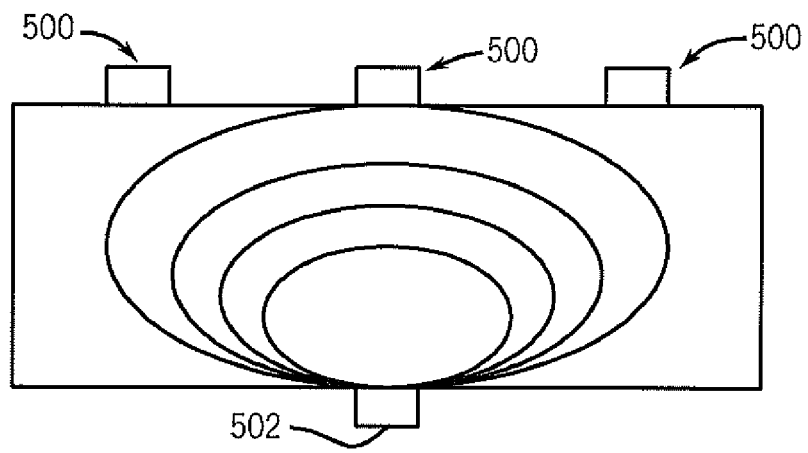

In some embodiments, as illustrated by FIGS. 6-8, multiple emitter and/or detector arrangements may be utilized in conjunction with one another to provide a transmission mode photon density wave system. Further, skewness metrics may be utilized with multiple emitter and/or detector arrangements to identify tissue characteristics and so forth. Specifically, FIG. 6 illustrates a first emitter 302 and a second emitter 304, wherein each of the emitters 302, 304 includes a red and an IR light source (e.g., LD). Waves 306 represent photon density waves propagating through tissue 307 from the emitters 302, 304 to a first detector 310 and a second detector 312. As will be understood by one of ordinary skill in the art, because the multiple emitters are generating separate waves in the same tissue bed, the waves can be made to interfere with one another by adjusting the modulation frequencies of each emitter 302, 304. Accordingly, multiple emitters may be utilized to steer intensities through the tissue and adjust intensity patterns in the different areas of tissue. For example, the phase of the photon density waves could be adjusted in such a way as to completely cancel out any signal at the first detector 310. Thus, if the first detector 310 detects a signal, it may be an indication of noise.

FIG. 7 illustrates an embodiment including multiple emitters 400 and a single detector 402 positioned adjacent a patient's tissue 404. This embodiment may be utilized to generate an adaptive constructive/destructive interference pattern in the tissue bed, including deep within the tissue bed, by adjusting the relative phases of the emitters (at a given wavelength) that would allow for the measurement of local tissue components. These would be visible in the phase and amplitude changes determined by the single detector.

In other embodiments utilizing multiple emitters, the interference of photon density waves may facilitate sweeping photon density waves through a probed volume by changing the relative phase between the emitters. For example, such techniques may be utilized to establish a "phased array" of photon density waves for use in pulse oximetry and hemometry techniques. Indeed, such a "phased array" technique may facilitate identification of regions rich with pulsatile signals in the probed tissue and/or calibration of a sensor through the interference of photon density waves. For example, the phases of individual waves may be controlled to determine the intensity profile within the medium.

It may be desirable to detect regions rich with pulsatile signals to facilitate obtaining a strong pulsatile signal. For example, it may be desirable to focus on a specific location in tissue that includes an artery or even a specific portion of the artery. The transmission mode arrangement may facilitate access to such specific locations by enabling deep penetration. Periodic sweeps may be performed to insure that the focus remains on the pulsation-rich regions. Further, such a technique may define an adaptive measurement system that may be utilized to identify regions of low saturation and/or regions in the probed tissue where blockage may result in anemic conditions. Additionally, it is believed that the use of multiple emitters may facilitate adaptation of the sensor to different physiological variations between patients, such as different skin and/or tissue characteristics. Such features may be used in conjunction with analysis of the skewness of detected photon distribution to obtain more accurate data regarding the observed tissue.

FIG. 8 illustrates an embodiment including multiple detectors 500 and a single emitter 502 capable of emitting and detecting photon density waves passed through tissue 504. The illustrated embodiment may be utilized to identify non-physiological artifact. Each of the multiple detectors 500 may have a different phase and amplitude relationship with respect to each other. Uncorrelated changes in phase and amplitude between the multiple detectors 500 would result in a non-physiological artifact such as noise artifact, sensor off, and so forth.

The inclusion of multiple detectors around a tissue bed may facilitate detection of and/or compensation for a variety of noise artifacts that typically plague existing pulse oximetry technologies. Indeed, for a given wavelength, a time-varying phase and amplitude relation between multiple detectors may be established which is correlated to arterial pulse. The phase and amplitude information may form a phase space that yields a bounded parameter space for a single wavelength that contains physiological measurements. Noise artifacts will typically lie outside of this bounded area, as will be discussed in further detail below. Further, the addition of a second wavelength may facilitate formation of a 4-dimensional physiological measurement space that facilitates noise artifact reduction due to constraints of decision planes in the hyperspace. Correlated phase and amplitude changes for a single wavelength are bounded by physiological parameters such as arteriole density, realistic hematocrit numbers, and so forth. At a single wavelength, these bounds result in bounds on the detected amplitude and phase in a 2D space. These same bounds are applicable for a second wavelength. The 4 factor correlation (phase(wavelength1), phase(wavelength2), amplitude(wavelength1), amplitude(wavelength2)) is bounded by physiological factors in a linked 4D space. The bounds can be drawn as hyperplanes in that space. For example, cluster analysis, Neural Networks, and partial least squares (PLS) algorithms may be used to generate the decision planes and compensate for a variety of noise artifact.

Figure 9:
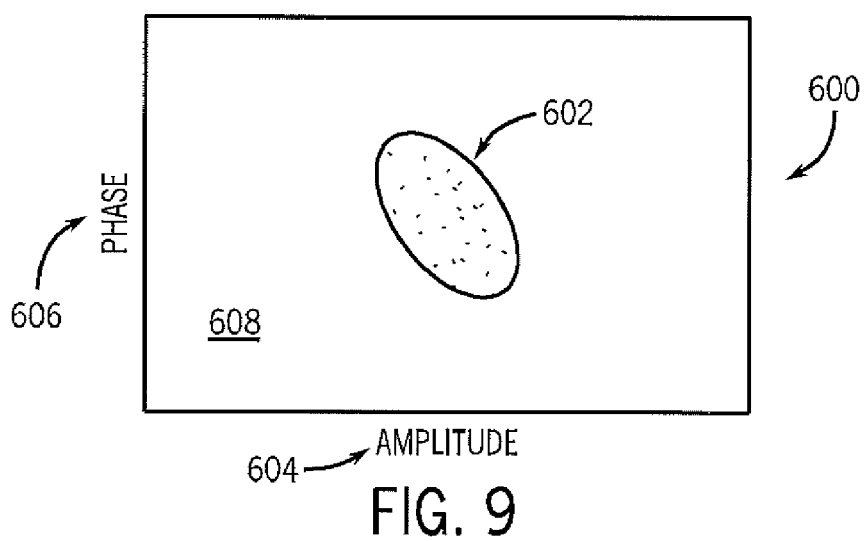
FIG. 9 illustrates a 2-dimensional plot that represents a physiological state characterized by amplitude and phase shifts in accordance with present embodiments.

In some embodiments, and as an example, FIG. 9 includes a 2-dimensional plot 600 that represents a physiological state 602 characterized by amplitude 604 and phase shifts 606.

Once phase shift and/or amplitude data has been properly characterized based on empirical data, certain correlations may be indicative of a change in pressure (e.g., a sensor is attached too tightly), a certain area of tissue being subject to exsanguination, a sensor being off, noise being present, and so forth. The plot 600 is representative of a single wavelength at a given frequency. Thus, multiple wavelengths at a given frequency would each have this type of physiological space for expected amplitude and phase variation. Noise artifact 608 will generally lie outside of this bounded parameter space or physiological regime. Accordingly, if a measurement falls outside of the physiological regime, it may be discarded as including too much noise. When a measurement is discarded, it may be replaced with the previous measurement or some combination of historical values, For example, historical values may be averaged using an averaging routine to provide a replacement for the noisy current measurement value.

What is claimed is:

1. A monitoring system, comprising:
an emission feature configured to emit light into tissue;
a modulator configured to modulate the emitter at a modulation frequency generally in a range of about 50 MHz to 3.0 GHz to generate a generally resolvable photon density waves;
a detection feature configured to detect photons of the photon density waves after passage through the tissue and configured to provide a distribution of detected photons over a time period for the photon density waves; and
a processor configured to calculate a skewness of the distribution and making determinations relating to a value of a physiologic parameter of the tissue based at least in part on the skewness of the distribution.

2. The system of claim 1, comprising a memory storing empirical data, wherein the processor is configured to analyze the skewness by comparing the skewness to the empirical data stored in the memory.

3. The system of claim 2, wherein the empirical data comprises skewness values for various vascular disease conditions of tissue.

4. The system of claim 1, wherein the detection feature comprises a signal processing device configured to provide the distribution by determining a derivative of a detected waveform of the photon density waves.

5. The system of claim 4, comprising a noise-reduction feature configured to enhance a single-to-noise level of the distribution via an ensemble averaging procedure.

6. The system of claim 5, wherein the noise-reduction feature is configured to trigger the ensemble averaging procedure based at least in part on a modulation waveform produced by the modulator to modulate the emitter.

7. The system of claim 1, wherein the emission feature comprises a pair of laser diodes each configured to emit a different wavelength of light.

8. The system of claim 1, wherein the processor is configured to determine a blood oxygen saturation level based at least in part on an amplitude of the distribution.

9. The system of claim 1, wherein the detection feature comprises a photodetector disposed within a monitor and fiber optic cable coupled to a sensor body.

10. The system of claim 1, wherein the processor is configured to calculate an estimated number of scattering particles in the tissue based at least in part on detected phase shifts.

11. The system of claim 1, comprising a plurality of emitters, wherein the modulator is configured to modulate light from the plurality of emitters to generally sweep the tissue with a plurality of modulation frequencies.

12. A method of analyzing tissue, comprising:
modulating light from an emitter of a patient monitoring device at a modulation frequency in a range of about 50 MHz to 3.0 GHz to generate photon density waves;
transmitting the photon density waves into a medium;
detecting the photon density waves after passing through at least a portion of the medium;
providing a data distribution of detected photons over a time period for the photon density waves;
calculating a skewness of the data distribution;
providing a value of a physiologic parameter of the tissue based at least in part on the skewness of the data distribution.

13. The method of claim 12, comprising analyzing the skewness by comparing the skewness to previously acquired empirical data that is indicative of known tissue conditions.

14. The method of claim 12, wherein providing the data distribution comprises determining a derivative of a detected waveform of the photon density waves.

15. The method of claim 12, comprising enhancing a signal-to-noise level of the data distribution via an ensemble averaging procedure.

16. The method of claim 15, comprising triggering the ensemble averaging procedure based at least in part on the modulation frequency.

17. A pulse oximeter, comprising:
a modulation feature configured to modulate an emitter at modulation frequencies in a range of about 50 MHz to 3.0 GHz to produce photon density waves of red and infrared light;
a detector configured to detect the photon density waves after the photon density waves have passed through tissue and configured to use data acquired from detection of the photon density waves to output a photon density wave signal that is indicative of a number of photons detected over a time period;
analysis circuitry configured to calculate a skewness of the photon density wave signal that correlates to scattering of the photons in the tissue, wherein the analysis circuitry is configured to identify characteristics of the tissue based at least in part on a comparison of operational aspects of the modulation feature and the skewness of the photon density wave signal.

18. The pulse oximeter of claim 17, wherein the analysis circuitry comprises a processor configured to compare the skewness with established values to facilitate identification of certain characteristics of the tissue.

19. The pulse oximeter of claim 17, comprising a noise-reduction feature configured to enhance a signal-to-noise level of the distribution via an ensemble averaging procedure.

20. The pulse oximeter of claim 17, wherein the emitter comprises a non-sinusoidal emitter.

* * * * *